United States Patent [19]
Kupersmith et al.

[11] Patent Number: 5,050,601
[45] Date of Patent: Sep. 24, 1991

[54] CARDIAC DEFIBRILLATOR ELECTRODE ARRANGEMENT

[76] Inventors: Joel Kupersmith, 40 River Hill Rd., Louisville, Ky. 40207; Igor Singer, 5820 Orion Rd., Louisville, Ky. 40222

[21] Appl. No.: 529,312
[22] Filed: May 29, 1990
[51] Int. Cl.⁵ .................................... A61N 1/39
[52] U.S. Cl. ................. 128/419 D; 128/786
[58] Field of Search ......... 128/419 D, 419 P, 785, 128/786

[56] References Cited

U.S. PATENT DOCUMENTS

| | | | |
|---|---|---|---|
| 4,289,138 | 9/1981 | Halvorsen | 128/419 P |
| 4,774,952 | 10/1988 | Smits | 128/419 D |
| 4,922,927 | 5/1990 | Fine et al. | 128/786 |
| 4,944,300 | 7/1990 | Saksena | 128/419 D |

Primary Examiner—William E. Kamm
Assistant Examiner—Kennedy J. Schaetzle
Attorney, Agent, or Firm—McAulay, Fisher, Nissen, Goldberg & Kiel

[57] ABSTRACT

A cardiac defibrillator employs first and second catheters, each of which have individual coils wound thereon which operate as a cathode in a defibrillating system. Each of the catheters are pliable enough and has a small enough diameter so that both of them can be perveneously placed through the tricuspid valve into the right ventricle of a patient's heart. Each of the catheters has a small screw at the distal end to permit affixing the catheter to different points in the wall of the septum. The defibrillating coils are entirely within the right ventricle and have a relationship relative to one another such that the defibrillating pulse delivered simultaneously to the two coils provides a field that creates effective defibrillation at a relatively low energy level such as five to fifteen joules.

10 Claims, 1 Drawing Sheet

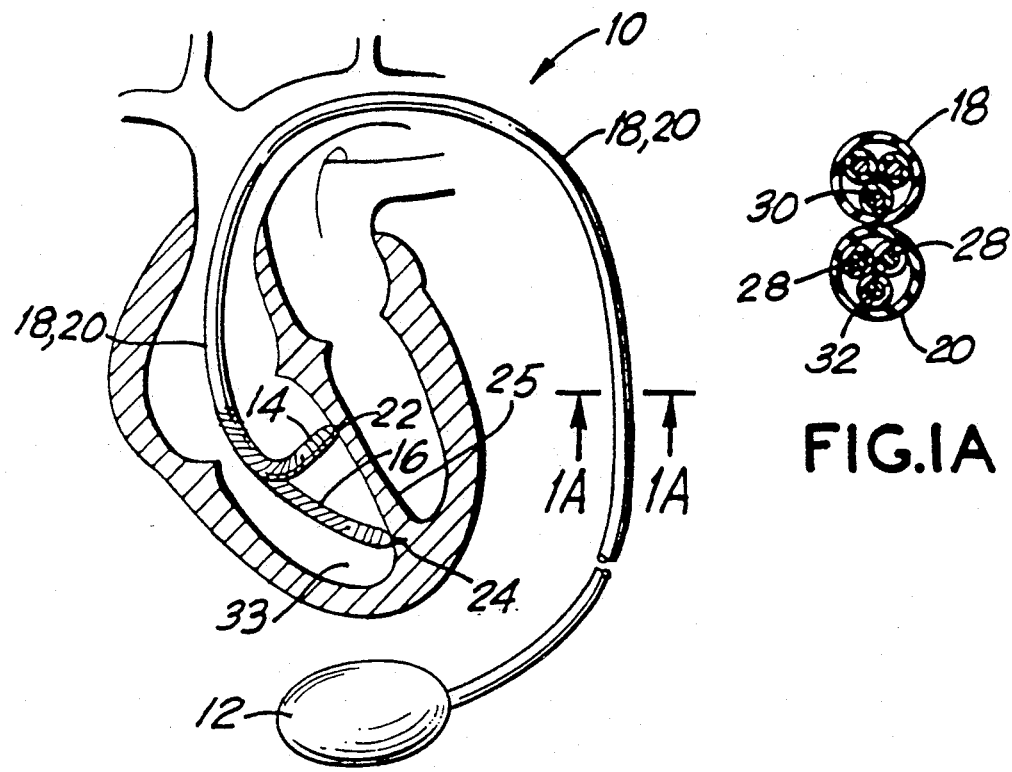
FIG.1A
FIG.1
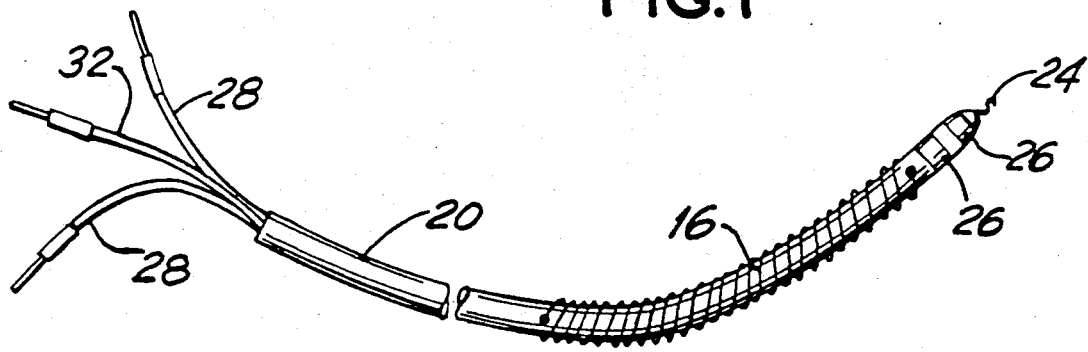
FIG.2

CARDIAC DEFIBRILLATOR ELECTRODE ARRANGEMENT

BACKGROUND OF THE INVENTION

The present invention relates to an improved implantable defibrillator.

Defibrillators ar electronic devices capable of delivering sufficient energy to the cardiac muscle to convert an erratic heart rhythm (ventricular fibrillation) to a normal heart rhythm. Defibrillators are used in a variety of situations where there is a possibility that a person may have life threatening ventricular arrhythmias (ventricular tachycardia or ventricular fibrillation).

It is known in the art that cardiac defibrillation may be achieved by applying electrodes to a person's skin, on either side of the heart, and applying electric energy to the electrodes. Such a system is used where the need for defibrillation is not foreseeable. However, in instances where the need for defibrillation is due to a pathological state, it is preferable to use an implantable defibrillation system that can automatically apply the necessary electrical discharge to the heart when the need arises.

Implantable defibrillators of the type above-mentioned are known in the art. These implantable defibrillators generally include an energy source, such as a battery, a capacitor to store energy for delivery to the heart and electrodes to deliver the energy to the heart. Additionally these systems include a sensor to determine when defibrillation is needed.

Pacemakers, in contrast to defibrillators, are electronic devices which pace the heart when the heart rate is too slow. Pacemakers, in contrast to defibrillators, use a small amount of energy. The energy requirement of a pacemaker is a fraction of the energy required to defibrillate the heart.

In presently known implantable defibrillator systems, ten to twenty-five joules of energy is necessary to defibrillate the heart. In order to achieve this energy delivery, fairly large components are needed. Thus it is currently necessary to open the chest to implant the defibrillator and place at least one electrode on the heart. This is major surgery requiring anesthesia and thus has attendant risks.

Major surgery creates risks which should be avoided when possible. This is of particular significance in a patient who is a candidate for an implantable defibrillation system since such patients are already in less than optimum health.

Accordingly it is an object of the present invention to provide an implantable defibrillator which does not require open-chest surgery for implantation.

It is yet another object of the present invention to provide such an implantable defibrillator which can defibrillate the heart using less energy than previously known defibrillators. That is, the purpose is to lower the defibrillation threshold.

BRIEF DESCRIPTION

In one embodiment of the cardiac defibrillator of this invention, the case of the pulse generator operates as an anode. The cathode is composed of first and second electrode terminals. These first and second electrode terminals are electrical coils mounted near the distal end of first and second catheters respectively. The catheters are sufficiently pliable and sufficiently small in diameter so as to be perveneously placed and traverse the tricuspid valve to enter the right ventricle. A small extractable screw at the distal end of each of the two catheters permits affixing each catheter to the septum. One catheter is affixed at the lowest part of the septum wall and the other at the uppermost part of the septum wall.

A pair of sensing electrodes adjacent to the screw of one of the two catheters provides a signal of heart function. When the signal indicates fibrillation, the electrical circuitry in the anode case responds by discharging the energy stored in a capacitor as a pulse of electrical energy to the two catheter coils. The result is to provide a pulse of energy that is well distributed over the heart so as to provide a defibrillation function. Because of the positioning of the two catheters and in particular the resultant positioning of the two cathode coils, the total amount of energy needed to defibrillate is less than previously required and in particular, in one embodiment, was five joules of total energy.

THE FIGURES

FIG. 1 is a schematic showing of two catheters placed perveneously in the right ventricle and attached to the septum.

FIG. 1A is a sectional view along the plane 1A—1A in FIG. 1. FIG. 1A is at a larger scale than is FIG. 1.

FIG. 2 is a longitudinal view of one of the two catheters shown in FIG. 1. The two catheters are the same in structure.

DESCRIPTION OF THE PREFERRED EMBODIMENTS

The drawings are at different scales and refer to the same embodiment. The defibrillator 10 produces sufficient energy to convert an erratic heart rhythm (ventricular fibrillation) to a normal heart rhythm. The defibrillator 10 is intended for relatively permanent implantation in a patient. It is used where the need for defibrillation is due to a pathological state. Sensing electrodes in the defibrillator monitor the electrical signals generated in the heart. The defibrillator responds to a predetermined type of signal indicating ventricular fibrillation by automatically applying the required pulse of electrical energy to stop the erratic heart rhythm and to reestablish a normal heart rhythm.

The case of the pulse generator 12 serves as the anode. Alternately, a separate subcutaneous patch which is connected to the pulse generator 12 can be employed as the anode. The cathode is comprised of two separate coils 14 and 16 which are mounted near the distal end of two catheters 18, 20 respectively. These coils 14, 16 are preferably platinum-iridium coils. An extractable mounting screw 22, 24 is positioned at the distal end of each of the two catheters 18 and 20. These mounting screws 22, 24 are affixed to the inner wall of the heart and specifically to the septum 25. They serve to position and hold the catheters in place thereby assuring the positioning of the defibrillator cathode terminals 14 and 16.

Adjacent to the extractable screw 24 on the catheter 20 are two annular electrode terminals 26. These terminals 26 are circular rings mounted on the outside of the catheter 20 sheath and are connected by lead lines 28 that run through the catheter 20 to electronic circuity in the case 12. These annular electrode terminals 26 are in physical contact with heart tissue because they are adjacent to the screw 24 which is attached to the septum 25. As a consequence, they pick up sufficient electrical signal from heart activity to provide an indication of the normal heart condition. When that condition changes so as to indicate fibrillation, the circuitry in the pulse generator 12 responds in a known manner by providing the necessary electrical energy as a pulse to the electrode terminal coils 11 and 16 that restores normal heart rhythm and prevents fibrillation. Thus the terminals 26 constitute sensing terminals. The operation of the sensing terminals to provide a signal that kicks in the fibrillation defeating pulse is a known technique in this art and the electronics involved need not be disclosed further herein.

A similarly positioned pair of annual pacemaker electrode terminals on the outer surface of the catheter 18 can be used to perform a pacemaking function in a known fashion.

The sensing electrode terminals 26 are preferably positioned near the distal end of the catheter 20 that is connected to the lower portion of the septum and thus the pacemaking electrode terminals are preferably positioned on the catheter 18 which is connected to the upper portion of the septum.

The cathode electrical terminals are in the form of coils 14 and 16. Their positioning is important. These coils 14, 16 are wound on the outside of the catheters 18 and 20 and are connected to the pulse generator 12 through leads 30, 32 which extend through the catheter 18, 20 sheaths back to the electrical circuity in the generator 12. These coils 14 and 16 are positioned in the right ventricle 33 and thus are in contact with the blood in the ventricle and through the blood are electrically coupled to the heart tissue of the ventricle. It has been found important that the distal ends of the catheters 18 and 20 be positioned, one at the lower end of the septum (the right ventricular apex) and the other at the top of the septum (the right ventricular outflow tract). It has been found that when a defibrillation pulse is applied to the two coils 14 and 16, a more efficient defibrillation is achieved when they have such a relation to the septum and thus less total energy can be employed to provide the desired defibrillation.

To achieve this positioning of the coils 14 and 16, the catheters 18 and 20 are each flexible, small diameter devices having a diameter preferably in the range of 6.5 to 8.0 French. Such catheters can be passed through the tricuspid valve and can be placed, one (the catheter 18) in the right ventricular outflow tract and one (the catheter 20) at the ventricular apex. This provides the arrangement where a pulse of approximately five to ten joules of energy is usually enough to defibrillate. The energy required to defibrillate is very much a function of the individual heart. The point of this invention is to provide a technique for minimizing the energy required for a given patient. Thus in some cases the threshold energy for defibrillation using this invention may be as high as fifteen joules.

FIG. 1 is a highly schematic view of the heart in which the right ventricle 33 is schematically shown. The two coils 14 and 16 are shown positioned in a fashion which suggests the typical desired geometric relationship between the two coils when the catheters 18 and 20 are affixed in the approximate position shown. That is, the average axis of the coil 14 and the average axis of the coil 16 are such that the typical angle between these two average axes is between forty-five and sixty degrees. This angular relationship has a significant effect on the resultant field generated by the pulse which is simultaneously delivered by the two defibrillating coils 14, 16. It is believed that the resultant field provides more effective defibrillation because of this angular relationship.

It is believed that an optimum field from the point of view of minimizing the amount of energy required to effect defibrillation is created if the anode is in the form of a subcutaneous patch positioned under the skin overlying the cardiac apex. The cardiac apex is at the septum wall where screw 24 is connected to the heart tissue as shown in FIG. 1.

In one embodiment, the cathode coils 14 and 16 were each 15,000 turns of platinum iridium wire having a three mil (0.003 inch) gage, wound with one millimeter spacing to form coils each six centimeters in length. The diameter of each catheter where the coil is wound is 7.0 French. The distal end of each coil 14, 16 is about one centimeter from the end of the catheter. The annular electrodes 26 are within that one centimeter length.

The electrical circuity in the pulse generator 12 includes a battery, a capacitor across the terminals of the battery, and various switches. This circuity is of a known type to perform the functions required in a defibrillator of responding to an appropriate signal from the sensing electrodes 26 by providing a defibrillating pulse of electrical energy to the cathode coils 14 and 16. A typical defibrillating pulse that has been tested is the known biphasic pulse employed in this art. Since this electrical structure function is known and is described in the art, there is no need to describe it in any greater detail herein. A disclosure of such circuity may be found in U.S. Pat. No. 4,796,630 issued Jan. 10, 1989 and U.S. Pat. No. 4,825,871 issued May 2, 1989.

What is claimed is:

1. In an implantable cardiac defibrillator having an implantable pulse generator, a case connected to a first pole of said implantable pulse generator and having within the case means for delivering a predetermined defibrillating pulse of energy in response to a predetermined sensor signal indicating fibrillation, the improvement comprising:

first and second catheters, first and second defibrillating electrodes, said defibrillating electrodes being carried on the distal portions of respective ones of said first and second catheters and connected by lead wires through said catheters to a second pole of said pulse generator, each of said catheters being sufficiently pliable and having diameters sufficiently small to permit perveneously placing said catheters through the tricuspid valve into the right ventricle of a patient's heart, each of said catheters containing extractable fixing means at the distal ends thereof to permit affixing the distal ends of each of said catheters in the wall of the septum at predetermined positions along the wall of the septum, whereby defibrillation may be achieved with minimal energy.

2. The defibrillator of claim 1 wherein said first and second catheters have a diameter between 6.5 and 8.0 French.

3. The defibrillator of claim 1 wherein said extractable means are screw elements.

4. The defibrillator of claim 2 wherein said extractable means are screw elements.

5. The defibrillator of claim 1 wherein said energy required to defibrillate is between five and fifteen joules.

6. The defibrillator of claim 1 wherein said first and second defibrillating electrodes are positioned sufficiently close to the distal end of their respective ones of said catheters and have a length such that when the catheters are affixed to the wall of the septum, said electrodes are contained entirely within the right ventricle.

7. The defibrillator of claim 6 wherein said electrodes are coils mounted on the outer surface of said catheters and have an axial length of approximately six centimeters each.

8. The method of implanting cardiac defibrillation electrodes comprising the steps of:
 providing first and second defibrillating electrodes at the distal ends of first and second catheters respectively wherein each of said catheters are sufficiently pliable and have sufficiently small diameters to permit perveneously placing said catheters through the tricuspid valve into the right ventricle of a patient's heart,
 affixing the distal end of a first one of said catheters to the wall of the septum at the right ventricle outflow tract,
 affixing a second one of said catheters to the wall of the septum at the ventricular apex,
 positioning the distal ends of said catheters which carry said defibrillating electrodes in the right ventricle such that the defibrillating electrodes have average axes which are at a substantial angle to one another.

9. The method of claim 8 wherein said substantial angle is between forty-five and sixty degrees.

10. The method of claim 8 further comprising the step of:
 affixing an electrode which is a pole opposite from said defibrillating electrodes to the patient at a point overlying the cardiac apex of the patient's heart.

* * * * *